US00PP24689P2

(12) United States Plant Patent
Probst

(10) Patent No.: US PP24,689 P2
(45) Date of Patent: Jul. 22, 2014

(54) ***COREOPSIS* PLANT NAMED 'MERCURY RISING'**

(50) Latin Name: ***Coreopsis* hybrid**
Varietal Denomination: Mercury Rising

(76) Inventor: Darrell R. Probst, Hubbardston, MA (US)

( * ) Notice: Subject to any disclaimer, the term of this patent is extended or adjusted under 35 U.S.C. 154(b) by 168 days.

(21) Appl. No.: 13/573,404

(22) Filed: Sep. 13, 2012

(51) Int. Cl.
*A01H 5/00* (2006.01)

(52) U.S. Cl.
USPC ..... Plt./417

(58) Field of Classification Search
CPC ..... A01H 5/025
USPC ..... Plt./417
See application file for complete search history.

*Primary Examiner* — June Hwu
(74) *Attorney, Agent, or Firm* — Penny J. Aguirre

(57) ABSTRACT

A new cultivar of hybrid *Coreopsis* named 'Mercury Rising' characterized by its exhibits large inflorescences with ray florets that are solid red in color throughout the growing season with white tips appearing when plants are grown under hot temperatures, its vigorous growth habit with healthy foliage, its low growing plant habit, spreading outward from above ground stems that are well branched, its reliably perennial growth habit and cold hardiness at least in U.S.D.A. Zone 5, and its very good resistance to powdery mildew and leaf spot.

2 Drawing Sheets

Botanical classification: *Coreopsis* hybrid.
Variety denomination: 'Mercury Rising'.

BACKGROUND OF THE INVENTION

The present invention relates to a new and distinct cultivar of *Coreopsis* plant, botanically of hybrid origin and known as *Coreopsis* 'Mercury Rising' and will be referred to hereinafter by its cultivar name, 'Mercury Rising'. The new cultivar of *Coreopsis* is an herbaceous perennial grown for landscape and container use.

The new invention arose from an ongoing controlled breeding program in Hubbardston, Mass. The objective of the breeding program is to develop hybrid cultivars of *Coreopsis* with unique and superior garden attributes. In particular, to develop cultivars that are long-lived, sturdy, exhibit a true perennial habit and cold hardy to at least U.S.D.A Zone 5 in a wide range of flower colors and plant forms.

The Inventor made a controlled cross in summer of 2008 in his test garden in Hubbardston, Mass. between two unnamed plant from the Inventor's breeding program, the female parent is designated as G4 07-2 and the male parent is designated as Y 07-5. 'Mercury Rising' was selected in September 2009 as a single unique plant amongst the resulting seedlings.

Asexual reproduction of the new cultivar was first accomplished by stem cuttings under the direction of the Inventor in Kensington, Conn. in September of 2009. The characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Mercury Rising' as unique from all *Coreopsis* cultivars and species known to the Inventor.

1. 'Mercury Rising' exhibits large inflorescences with ray florets that are solid red in color with white tips appearing when plants are grown under hot temperatures.
2. 'Mercury Rising' exhibits a vigorous growth habit with healthy foliage.
3. 'Mercury Rising' exhibits a low growing plant habit, spreading outward from above ground stems that are well branched without the need for pinching.
4. 'Mercury Rising' exhibits a reliably perennial growth habit.
5. 'Mercury Rising' is cold hardy at least to U.S.D.A. Zone 5.
6. 'Mercury Rising' is shown very good resistance to powdery mildew and leaf spot.

The female parent differs from 'Mercury Rising' in having larger inflorescences that have a ray florets that are white in color with purple markings and in having a more open and less densely branched growth habit. The male parent differs from 'Mercury Rising' in being taller in height and in lacking cold hardiness in U.S.D.A. Zone 5. 'Mercury Rising' can be compared to *Coreopsis* cultivars 'Redshift' (U.S. Plant Pat. No. 20,412) and 'Center Stage' (U.S. Plant Pat. No. 22,707). 'Redshift' differs from 'Mercury Rising' in having inflorescences that are light yellow in color with a red eye for most of the season (turns more red in cool temperatures in fall) and in having a more upright plant habit. 'Center Stage' differs from 'Mercury Rising' in having a shorter bloom season, in being less cold hardy, and in being less disease resistant.

BRIEF DESCRIPTION OF THE DRAWING

The accompanying colored photographs illustrate the overall appearance and distinct characteristics of the new *Coreopsis*.

The photographs in FIG. 1 and FIG. 2 were taken of a plant of 'Mercury Rising' about one year in age as grown in a two-gallon container in a greenhouse in Mount Vernon, Wash.

Figure 3:
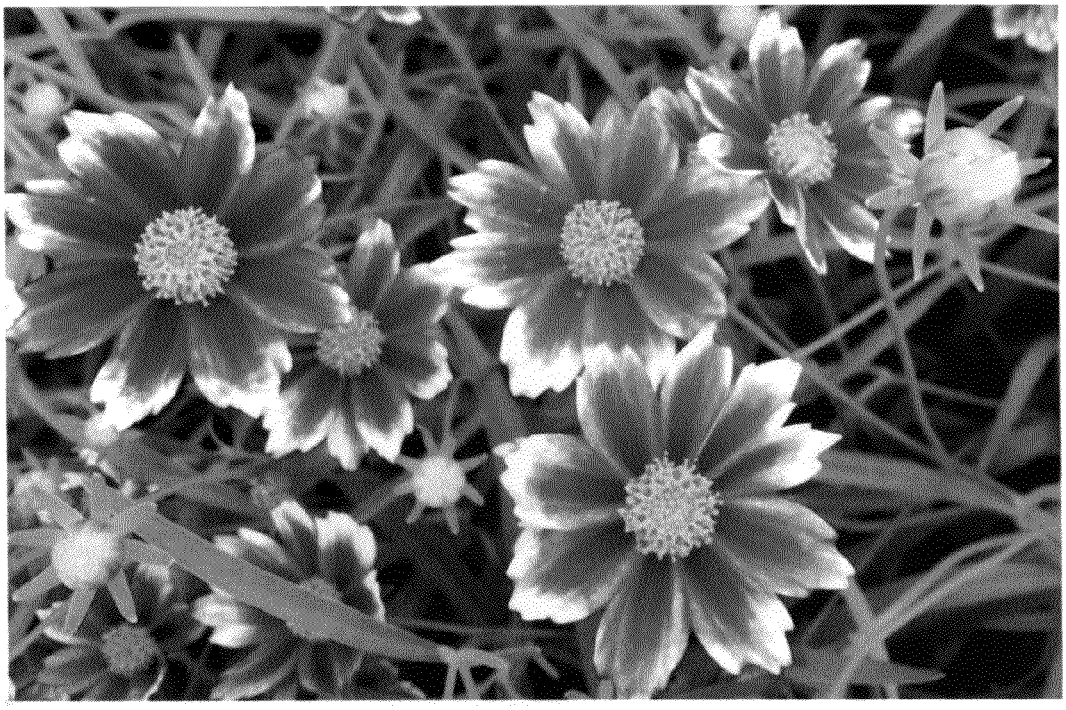

The photograph in FIG. 3 was taken of 4-week old plants as growing in 72-cell liners in Pace, Fla.

Figure 1:
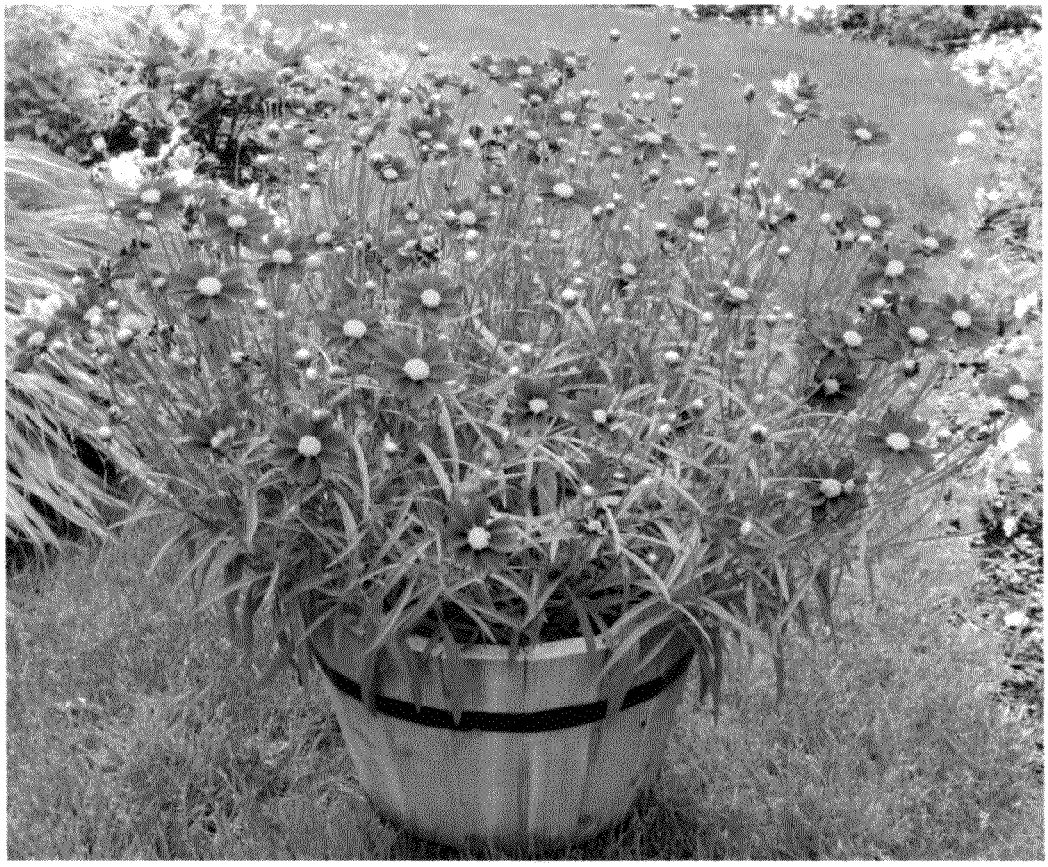

The photograph in FIG. 1 provides a view of the habit of 'Mercury Rising' in bloom.

Figure 2:
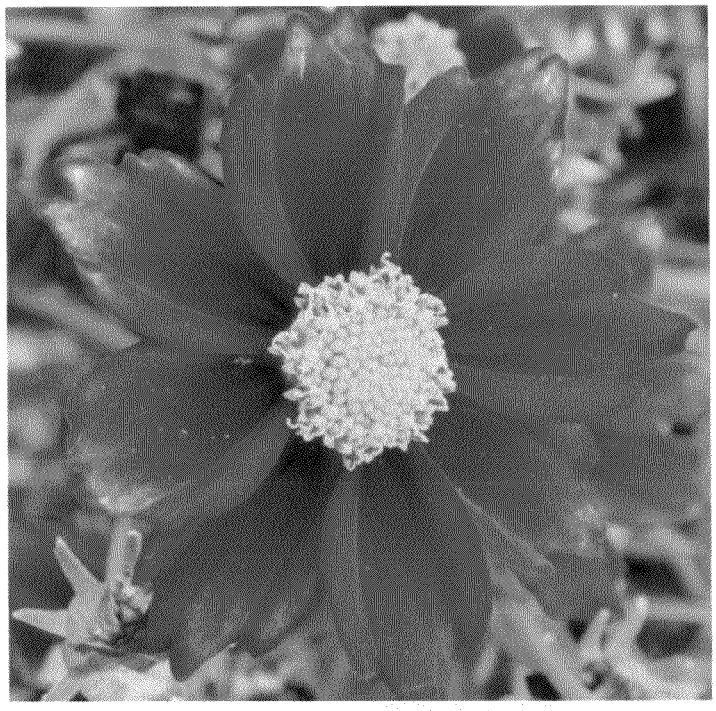

The photograph in FIG. 2 provides a close-up view of inflorescences of 'Mercury Rising'.

The photograph in FIG. 3 provides a view of inflorescences of 'Mercury Rising' as grown under hot temperatures. The colors in the photograph may differ slightly from the color values cited in the detailed botanical description, which accurately describe the colors of the new *Coreopsis*.

DETAILED BOTANICAL DESCRIPTION

The following is a detailed description of the new cultivar as observed for three years in a test garden in Hubbardston, Mass. with the detailed botanical data collected from six month-old plants of the new cultivar as grown in one-gallon containers in Kensington, Conn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms from June until hard frost in central Massachusetts.

*Plant habit*.—Herbaceous perennial, clump-forming, densely branched above ground stems that spread outward.

*Height and spread*.—Reaches about 45 cm in height in bloom and 90 cm in width on one year-old plants in the garden.

*Cold hardiness*.—At least in U.S.D.A Zone 5.

*Diseases resistance*.—Has been observed to be highly resistant to powdery mildew and leaf spot.

*Root description*.—Fibrous when young, becoming fleshy with age.

*Propagation*.—Terminal stem cuttings.

*Growth rate*.—Vigorous, plugs develop quickly in a one-gallon container.

Stem description:

*Shape*.—Oval, ridged.

*Stem color*.—Between 144A and 137C.

*Stem size*.—Main stems; an average of 30 cm in length (excluding terminal peduncle) and 3 mm in width, secondary; average of 15 cm in length and 2.5 mm in width.

*Stem surface*.—Glabrous.

*Stem aspect*.—Outward.

*Branching habit*.—Well-branched, an average of 20 main branches, 4 secondary branches per main stem.

*Internode length*.—An average of 6 cm.

Foliage description:

*Leaf division*.—Simple.

*Leaf margins*.—Entire to trifid.

*Leaf size*.—Variable, up to 8 cm in length and 9 mm in width when entire, up to 10 cm in length and 6 cm in width when tri-fid.

*Leaf shape*.—Lanceolate when entire, lanceolate lobes when tri-fid.

*Leaf base*.—Truncate to stem.

*Leaf apex*.—Acute.

*Leaf venation*.—Pinnate, not prominent, matches leaf color on upper and lower surface.

*Leaf attachment*.—Sessile.

*Leaf arrangement*.—Opposite.

*Leaf surface*.—Glabrous on upper and lower surface.

*Leaf color*.—Young and mature upper surface; between 137A and N137C, young and mature lower surface; between 137B and 137C.

Inflorescence description:

*Inflorescence type*.—Composite with a single row of ray florets surrounding disk florets in the center, forming a radiant head, inflorescences are borne on branch terminals in loose corymbs.

*Lastingness of inflorescence*.—8 to 10 days until senescence of ray florets, longer in cool temperatures, bracts and disk florets are persistent.

*Fragrance*.—None detected.

*Quantity of inflorescences*.—An average of 50 per main branch.

*Inflorescence size*.—Corymbs; an average of 17 cm in width and height, composite; an average of 1.5 cm in depth and up to 4.5 cm in diameter with disk portion an average of 1 cm in diameter.

*Inflorescence buds*.—Average of 1.2 cm in depth and in diameter, spherical in shape, color; 12B at apex and blending into 144A at base, outer bracts a blend of 144A and 138A.

*Peduncle*.—Corymb; an average of 6 cm in length and 2.5 mm in width, glabrous surface, between 144A and 137C in color, composite; an average of 11 cm in length and 1.5 cm in width, between 144A and 137C in color, surface glabrous.

Involucral bracts:

*Bract number*.—Two rows of 8.

*Bract arrangement*.—Outer bracts are un-fused and held slightly upward, inner bracts surround receptacle with a campanulate form with apical portion un-fused, spreading, and held close to lower surface of ray florets.

*Bract size*.—Outer bracts; an average of 6 mm in length and 1.5 mm in width, inner bracts; up to 8 mm in length and 4 mm in width with free portion an average of 6 mm in length and 4 mm in width.

*Bract color*.—Inner bracts N144A with 144A blended at the base and outer bracts a blend of 144A and 138A.

*Bract texture*.—Glabrous on outer and inner surfaces of outer and inner bracts.

*Bract apex*.—Acute on outer and inner bracts.

*Bract base*.—Truncate on inner and outer bracts.

*Bract margins*.—Entire.

*Bract shape*.—Outer bracts; lanceolate, inner bracts; narrowly elliptic.

Ray florets (sterile):

*Number*.—An average of 8 arranged primarily in one row.

*Shape*.—Oblong.

*Size*.—An average of 1.7 cm in length and 9 mm in width.

*Apex*.—2 to 3 notched.

*Base*.—Broadly cuneate.

*Margins*.—Entire with apex notched.

*Aspect*.—Held horizontal to slightly upward.

*Texture*.—Glabrous on inner and outer surfaces.

*Color*.—Opening and mature upper surface; darker than 59A with a slight blending of 60A, apex is NN155D in color when plants are grown under hot temperatures with the amount of apex coloration increasing in extreme heat, lower surface; margins 158A with centers 61A and thin margin of 61A.

Disk florets (perfect):

*Shape*.—Tubular, corolla is fused, flared at apex.

*Number*.—About 200.

*Size*.—About 9 mm in length and 1 mm in width.

*Color*.—En masse; 24A, corolla; base of tube is 18B in color, flared portion is 24A and translucent.

*Receptacle*.—About 5 mm in diameter and 2 mm in depth, 145C in color.

Reproductive organs:

*Presence*.—Disk flowers are perfect, ray florets are sterile.

*Gynoecium*.—1 Pistil, 7 mm in length, style is very fine and about 18A in color and translucent, bifid pilose stigma is 19A in color with branches about 0.7 mm in length and recurved, ovary is 1.5 mm in length, 0.5 mm in width, inferior, and 145B in color.

*Androcoecium*.—5 stamens, fused into tube surrounding style, 2 mm in length and 0.5 mm in width, about 164A in color, pollen is low in quantity and 24A in color.

*Fruit/seed*.—No fruit or seed development was observed.

It is claimed:

1. A new and distinct cultivar of *Coreopsis* plant named 'Mercury Rising' as herein illustrated and described.

* * * * *